United States Patent [19]

Neiss et al.

[11] Patent Number: 4,749,698

[45] Date of Patent: Jun. 7, 1988

[54] ANTIHYPERTENSIVE DERIVATIVES

[75] Inventors: Edward S. Neiss, New Canaan; John T. Suh, Greenwich, both of Conn.; John R. Regan, Mamaroneck, N.Y.; Jerry W. Skiles, Tuckahoe, N.Y.; Jeffrey N. Barton, New York, N.Y.; James J. Mencel, Norwalk, Conn.; Paul Menard, Tuckahoe, N.Y.

[73] Assignee: Rorer Pharmaceutical Corporation, Fort Washington, Pa.

[21] Appl. No.: 752,695

[22] Filed: Jul. 8, 1985

[51] Int. Cl.$^4$ ............... C07D 207/12; C07D 207/14; C07D 207/24; C07D 417/12; C07D 403/12; A61K 31/54; A61K 31/505; A61K 31/40; A61K 31/495

[52] U.S. Cl. .................................. 514/223.2; 548/527; 548/517; 548/518; 548/523; 548/524; 548/336; 548/327; 548/533; 548/537; 548/538; 548/470; 544/296; 544/284; 544/287; 544/331; 544/332; 544/122; 544/128; 544/139; 544/141; 544/131; 544/12; 544/13; 544/288; 546/140; 546/141; 546/143; 546/146; 546/153; 546/157; 546/158; 546/159; 546/162; 546/164; 546/174; 546/172; 546/165; 546/256; 546/273; 546/281; 514/19; 514/18; 514/259; 514/275; 514/307; 514/308; 514/333; 514/309; 514/310; 514/212; 514/313; 514/314; 514/338; 514/339; 514/341; 514/343; 514/394; 514/395; 514/397; 514/422; 514/423; 514/229; 514/228; 514/230; 514/232; 514/233; 514/234; 514/236; 514/414; 514/259; 260/998.2

[58] Field of Search ............... 548/533, 537, 538, 524, 548/470, 527, 517, 518, 523; 514/18, 19, 423, 414, 222, 259; 544/12, 13, 287, 284, 288, 296, 331, 332, 131, 122, 128, 139, 141; 546/256, 273, 281; 260/998.2

[56] References Cited

U.S. PATENT DOCUMENTS

| | | | |
|---|---|---|---|
| 4,431,644 | 2/1984 | Smith et al. | 544/13 |
| 4,431,645 | 2/1984 | Smith et al. | 544/13 |
| 4,468,396 | 8/1984 | Magatti | 544/13 |
| 4,514,391 | 4/1985 | Gordon et al. | 548/409 |
| 4,524,212 | 6/1985 | Gordon et al. | 548/409 |
| 4,559,340 | 12/1985 | Neustadt et al. | 544/13 |

Primary Examiner—John M. Ford

[57] ABSTRACT

Compounds having the general structure

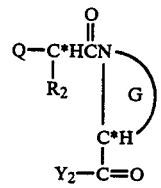

and their pharmaceutically acceptable salts, wherein the substituents are defined herein, which exhibit antihypertensive activity.

35 Claims, No Drawings

ANTIHYPERTENSIVE DERIVATIVES

BACKGROUND OF THE INVENTION

This application relates to compounds, their pharmaceutically acceptable salts, and pharmaceutical preparations made therefrom, having utility in the treatment of hypertension in subjects suffering therefrom.

SUMMARY OF THE INVENTION

Broadly stated, the present invention comprises compounds of the formula (1)

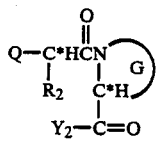
(1)

and its pharmaceutically acceptable acid addition, alkali and alkaline earth metal salts, wherein Q is $Y_1$—C(O)—C*H($R_1$)NH—, —$NH_2$, $R_1$—C(O)S(C*H($R_1$))$_{0-1}$—, or HS—(C*H($R_1$))$_{0-1}$;

$Y_1$ and $Y_2$ are independently —OH, —OR, or —$NR_1R_2$;

G is

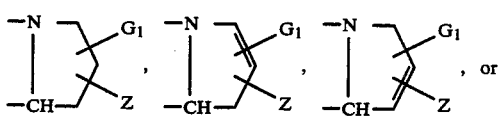

in which $G_1$ is H, —OH, $C_{1-6}$ alkyl, or $C_{1-6}$ alkoxy, $X_1$ and $X_2$ are independently a chemical bond or an alkylene bridge 1, 2 or 3 carbon atoms in length, provided that the ring which contains $X_1$ and $X_2$ contains 4 to 6 carbon atoms; one or both of $X_1$ and $X_2$ is optionally substituted with —OH, $C_{1-6}$ alkyl, or $C_{1-6}$ alkoxy; one of $X_1$ and $X_2$ is substituted with Z; $X_1$ and $X_2$ are otherwise substituted with hydrogen; and T is a saturated, unsaturated, or aromatic hydrocarbon ring with 5 to 7 carbon atoms;

Z is =CH—(alk)—M, =CH—(alk)C(O)—(alk)—M, =N—(alk)—M, —(alk)—CH=CH—(alk)—M, =N—(alk)—$SO_2$M, —(alk)—M, —(alk)—$SO_2$M, —(alk)—N($R_3$)—(alk)—M, —(alk)—O—(alk)—M,

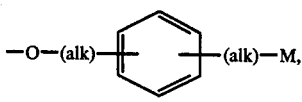

—(alk)—C(O)—(alk)—M, —(alk)—N($R_3$)—C(O)—(alk)—M, (alk)—C(O)—N($R_3$)—(alk)—M, —(alk)—N($R_3$)$SO_2$—(alk)—M, —(alk)—$SO_2$N($R_3$)—(alk)—M, —(alk)—N($R_3$)—(alk)—N($R_3$)—(alk)—M, —(alk)—N($R_3$)—(alk)—N($R_3$)—(alk)—C(O)—M, or —O—(alk)—C(O)—M, wherein (alk) is a chemical bond, an alkyl chain of the formula —($C_iH_{2i}$)—, or an alkyl chain of the formula —($C_iH_{2i-1}$)— which is substituted with a straight or branched alkyl group having 1 to 4 carbon atoms, wherein i is 1 to 6;

M is

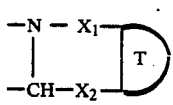

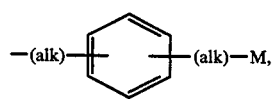

wherein A, B and E are independently H, $C_{1-6}$ alkyl, phenyl, benzyl, phenoxy, nitroalkylamino, alkanoylamino, alkanoylaminoalkyl, nitro, —OCH$_2$COOH, halogen, hydroxy, —CF$_3$, —SR, —OR, —NR$_1$R$_2$, —C(O)NR$_1$(R$_2$), —C(O)Y$_1$, —SO$_2$R, —SO$_2$NR$_1$R$_2$, or furfurylamino, provided that at least one of A and B is not hydrogen; and R, $R_1$, $R_2$, and $R_3$ in each occurrence, are independently hydrogen, alkyl having 1 to 8 carbon atoms, aryl having up to 12 carbon atoms, aryl-alkyl wherein the aryl moiety has up to 10 carbon atoms and the alkyl moiety has 1 to 6 carbon atoms, fused cycloalkylaryl having 8 to 12 carbon atoms, heterocyclic, or an alkyl group having 1 to 6 carbon atoms which is substituted with —NH$_2$, —NH—C(NH$_2$)=NH, or —NHC=NCH=CHCH=N;

wherein the alkyl, cycloalkyl, aryl, and fused arylcycloalkyl groups may carry substituents selected from the group consisting of alkoxy with 1 to 6 carbon atoms, —CF$_3$, —OH, —SH, halogen, —NO$_2$, and —COOR.

DETAILED DESCRIPTION OF THE INVENTION

Preferred substituents within the scope of the present invention include those wherein $Y_1$ and $Y_2$ are independently hydroxy or alkoxy containing up to 8 carbon atoms;

$R_1$ is H; alkyl having 1 to 8 carbon atoms; phenylalkyl wherein the alkyl has 1 to 4 carbon atoms, and more preferably phenethyl; or indanyl, e.g. 2-indanyl;

$R_2$ is H; alkyl having 1 to 8 carbon atoms; or an alkyl group having 1 to 8 carbon atoms, which is substituted with amino or an amino derivative such as

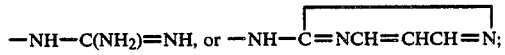

and $R_2$ is more preferably —$CH_3$ or $NH_2(CH_2)_4$—.

In the preferred embodiment, ring G is proline, or a proline ring containing one carbon-carbon double bond. In a preferred embodiment when G forms a fused ring system, $X_1$ and $X_2$ and T form tetrahydroquinoline or tetrahydroisoquinoline, or $X_1$ and $X_2$ form a proline ring. The proline ring of the one-ring or two-ring system G is preferably unsubstituted or substituted with an $R_3$ group which is preferably —OH or alkyl containing 1 to 6 carbon atoms.

When the chain connecting the moiety M to the ring includes a —$(CH_2)_i$-linkage where i is non-zero, one of the carbon atoms of that linkage can be substituted with a straight-chained or branched alkyl group of up to 6 carbon atoms. Preferred connecting chains Z include those attached at the ring G by a double bond; —NH—; —$NHSO_2$—; —NHC(O)—; —$CH_2NHC(O)$—; —NHNHC(O)—; —$N(CH_3)$ $CH_2$—; —$OCH_2CH_2$—; —$CH_2CH_2$—; —$N(CH_3)CH_2CH_2$—; and —NHC(O)$CH_2$.

A is preferably —$NH_2$; —OH; —$OCH_2COOH$; phenoxy; furfurylamino; alkoxy having up to 6 carbon atoms; or —$SO_2NR_1R_2$ wherein $R_1$ and $R_2$ are hydrogen, methyl, or $C_{2-3}$ alkyl, and more preferably —$SO_2NH_2$.

B is preferably halogen, and more preferably chloro; —$CF_3$; or —$SO_2NR_1R_2$ wherein $R_1$ and $R_2$ are hydrogen, methyl, or $C_{2-3}$ alkyl, and more preferably —$SO_2NH_2$; and E is preferably halogen or hydrogen.

The alkyl groups in general include straight-chained and branched groups, including methyl, ethyl, propyl, isopropyl, butyl, isobutyl, tert-butyl, amyl, iso-amyl, hexyl, and the like. By "halogen" is meant chloro, bromo, iodo, and fluoro.

Preferred substituents for $R_1$ and/or $R_2$ also include cycloalkyl groups, aryl groups, heterocyclic groups, and fused aryl-cycloalkyl groups, as defined herein. The preferred cycloalkyl groups include cyclopropyl, cyclobutyl, cyclopentyl, cyclohexyl, cycloheptyl, adamantyl, or norbornyl. The preferred aryl and fused aryl-cycloalkyl groups include phenyl, indolyl, indolinyl, indanyl, naphthyl, tetrahydronaphthyl, and decahydronaphthyl. Preferred heterocyclic groups include pyridyl, quinolyl, isoquinolyl, tetrahydroquinolyl, tetrahydroisoquinolyl, decahydroquinolyl, decahydroisoquinolyl, pyrrolidyl, pyrrolyl, morpholinyl, furyl, tetrahydrofuryl, furfuryl, benzimidazolyl, thienyl, and imidazolyl. Preferred aryl-alkyl substituents include benzyl and phenethyl. Preferred substituents on the alkyl, cycloalkyl, aryl, and fused aryl-cycloalkyl substituents include alkyl and alkoxy with 1 to 6 carbon atoms, —$CF_3$, —OH, —$NH_2$, phenoxy, —$NR_1R_2$, —COOH, —CN, —SH, halogen, —$NO_2$, and COOR, particularly COO—$C_{1-6}$ alkyl.

Compounds according to formula (1) can contain asymmetric centers at the carbon atoms marked thus: C*. Each of these carbon atoms can have an (R) or an (S) configuration, and preferably (S). Individual optical diastereoisomers as well as mixtures thereof are considered to be within the scope of this invention. When diastereoisomeric products result from the synthetic procedures, the desired diastereoisomeric product can be separated by conventional chromatographic or fractional crystallization methods.

The compounds of formula (1) can be prepared by coupling compounds of formulas (2) and (3)

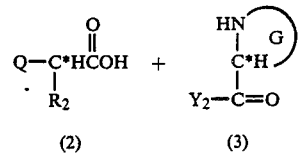

(2)    (3)

in which the substituents on ring G, including Z, are previously present or are subsequently attached. The various substituents on compounds (2) and (3) have been defined above.

It will be recognized by those skilled in this art that the coupling of compounds (2) and (3) can be carried out by conventional peptide linkage techniques, e.g. in the presence of a coupling agent such as DCC (N,N'-dicyclohexylcarbodiimide) or CDI (N,N'-carbonyldiimidazole). Alternatively, one may prefer to convert the —COOH group of compound (2) to —C(O)Cl, and then react the resulting intermediate with compound (3). Alternatively one may preferably convert the compound (2) to the corresponding N-carboxyanhydride (NCA) by allowing (2) to react with phosgene, and then react the resulting N-carboxyanhydride with compound (3) to yield the desired intermediate. It will further be recognized that the nitrogen atom which is between the carbon atoms to which $R_1$ and $R_2$ are attached can be protected with a blocking group such as 2,2,2-trichloroethoxycarbonyl or benzyloxycarbonyl. The protecting group is subsequently removed, preferably after compounds (2) and (3) have been joined together. Other nitrogen atoms, in substituents such as $NH_2(CH_2)_4$—, should be protected and then deprotected in a similar manner. Similarly, $Y_1$ and $Y_2$ are preferably converted to ethoxy, t-butoxy, or benzyloxy, before the intermediates are reacted. If the free acid is desired, it is subsequently obtained by removal of the esterifying group in a known manner.

The compounds of the present invention in which one of $Y_1$ and $Y_2$ is —OH and the other is alkoxy, such as methoxy or ethoxy, are preferably made by reacting compounds (2) and (3) as shown above in which one of $Y_1$ and $Y_2$ is the desired alkyl ester, and the other is an easily cleaved ester group such as t-butoxy. The amide intermediate thus prepared yields upon a mild acid hydrolysis the desired monoester-monoacids.

When Q contains sulfur, the preferred synthetic route is via the acid chloride.

The compounds of this invention form salts with various inorganic and organic acids and bases which are also within the scope of the invention. Such salts include ammonium salts, alkali metal salts like sodium and potassium salts (which are preferred), alkaline earth metal salts like the calcium and magnesium salts, salts with organic bases e.g., dicyclohexylamine salts, N-methyl-D-glucamine, salts with amino acids like arginine, lysine and the like. Also, salts with organic and inorganic acids may be prepared, e.g., HCl, HBr, H₂SO₄, H₃PO₄, as well as methanesulfonic, toluenesulfonic, maleic, acetic, malic, citric, fumaric and camphorsulfonic acids. The non-toxic physiologically acceptable salts are preferred, although other salts are also useful, e.g., in isolating or purifying the product.

The salts may be formed by conventional means, as by reacting the free acid or free base forms of the product with one or more equivalents of the appropriate base or acid in a solvent or medium in which the salt is insoluble, or in a solvent such as water which is then removed in vacuo or by freeze-drying, or by exchanging the cations of an existing salt for another cation on a suitable ion exchange resin.

The action of the enzyme renin on angiotensinogen, a pseudoglobulin in blood plasma, produces the decapeptide angiotensin I. Angiotensin I is converted by angiotensin converting enzyme (ACE) to the octapeptide angiotensin II. The latter is an active pressor substance which has been implicated as the causative agent in various forms of hypertension in various mammalian species, e.g., rats and dogs. The compounds within the scope of this invention which intervene in the renin —to—angiotensin I —to— angiotensin II sequence inhibit angiotensin I converting enzyme and therefore are useful in reducing or relieving hypertension.

Furthermore, the compounds within the scope of the present invention which possess diuretic activity promote relief from hypertension by promoting diuresis, and consequently have utility in treating congestive heart failure. Compounds within the scope of this invention can also simultaneously possess ACE inhibitory and diuretic activity, which is particularly unexpected in view of the fact that such simultaneous activity cannot be predicted from prior art compounds. Thus by the administration of a composition containing one or a combination of compounds of formula (1) or pharmaceutically-acceptable salts thereof, hypertension in the species of mammal suffering therefrom is alleviated. A single dose, or preferably two to four divided daily doses, provided on a basis of about 0.1 to 100 mg per kilogram per day, preferably about 1 to 50 mg per kilogram per day, is appropriate to reduce blood pressure. The substance is preferably administered orally, but a parenteral route such as subcutaneously, intramuscularly, intravenously or intraperitoneally can also be employed.

The compounds of this invention are also indicated for use in reducing intraocular pressure, i.e. for treating glaucoma. This effect is obtained by administering the amounts indicated above to a host in need of such treatment.

The compounds of the invention can be utilized by formulating one or more of them in compositions such as tablets, capsules or elixirs for oral administration or in sterile solutions or suspensions for parenteral administration. About 10 to 500 mg of a compound or mixture of compounds of formula (1) or physiologically acceptable salt(s) thereof is compounded with a physiologically acceptable vehicle, carrier, excipient, binder, preservative, stabilizer, flavor, etc., in a unit dosage form as called for by accepted pharmaceutical practice. The amount of active substance in these compositions or preparations is such that a suitable dosage in the range indicated is obtained.

Illustrative of the adjuvants which may be incorporated in tablets, capsules and the like are the following: a binder such as gum tragacanth, acacia, corn starch or gelatin; an excipient such as dicalcium phosphate; a disintegrating agent such as corn starch, potato starch, alginic acid and the like; a lubricant such as magnesium stearate; a sweetening agent such as sucrose, lactose or saccharin; a flavoring agent such as peppermint, oil of wintergreen or cherry. When the dosage unit form is a capsule, it may contain in addition to materials of the above type a liquid carrier such as a fatty oil. Various other materials may be present as coatings or to otherwise modify the physical form of the dosage unit. For instance, tablets may be coated with shellac, sugar or both. A syrup or elixir may contain the active compound, sucrose as a sweetening agent, methyl and propyl parabens as preservatives, a dye and a flavoring such as cherry or orange flavor.

Sterile compositions for injection can be formulated according to conventional pharmaceutical practice by dissolving or suspending the active substance in a vehicle such as water for injection, a naturally occurring vegetable oil like sesame oil, coconut oil, peanut oil, cottonseed oil, etc., or a synthetic fatty vehicle like ethyl oleate, or the like. Buffers, preservatives, antioxidants and the like can be incorporated as required.

Specific embodiments of the invention are illustrated in the following Examples.

EXAMPLE 1

N-[N-[(1S)-1-(Hydroxycarbonyl)-3-phenylpropyl]-L-alanyl]-4-(2,4-disulfamoyl-5-chloroanilino)proline A mixture of N-[N-[(1S)-1-(ethoxycarbonyl)-3-phenylpropyl](2,2,2-trichloroethoxycarbonyl)-L-alanyl]-L-prolin-4-one ethyl ester (2 mmol), 4-amino-6-chloro-N,N'bis[(dimethylamino)methylene]-1,3-benzenedisulfonamide (3 mmol), sodium cyanoborohydride (5 mmol) and molecular sieves in absolute ethanol is stirred at room temperature for several days, filtered and the volatiles are removed in vacuo. The residue is purified by HPLC. The 2,2,2-trichloroethoxycarbonyl protecting group is removed with zinc and acetic acid and the esters and sulfonamide protecting groups are removed by reaction with alkali to provide the product.

EXAMPLE 2

N-[N-[(1S)-1-(Hydroxycarbonyl)-3-phenylpropyl]-L-alanyl]-4-[[(2-amino-4-chloro-5-sulfonyl]amino]proline To a mixture of N-[N-[(1S)-1-(ethoxycarbonyl)-3-phenylpropyl]-N-(2,2,2-trichloroethoxycarbonyl)-L-alanyl]-L-prolin-4-one ethyl ester (1 mmol) and 1-(N-(2,2,2-trichloroethoxycarbonyl)amino)-3-chloro-4,6-benzenedisulfonamide (2 mmol) and molecular sieves in absolute ethanol is added sodium cyanoborohydride (2 mmol) portionwise. The mixture is kept at room temperature for 24 hours and additional sodium cyanoborohydride (2 mmol) is added. The mixture is kept at room temperature 24 hours, filtered and the volatiles are removed in vacuo. Purification of the residue on HPLC and concentration of the product rich fractions provide the intermediate. The 2,2,2-trichloroethoxycarbonyl protecting groups are removed with zinc and acetic acid and the esters are hydrolyzed with alkali to furnish the product.

EXAMPLE 3

N-[N-[(1S)-1-(Hydroxycarbonyl)-3-phenylpropyl]-L-alanyl]-4-(2,4-disulfamoyl-5-chlorophenylimino)proline To a mixture of N-[N-[(1S)-1-(ethoxycarbonyl)-3-phenylpropyl]-N-(2,2,2-trichloroethoxycarbonyl)-L-alanyl]-L-prolin-4-one ethyl ester (20 mmol), 4-amino-6-chloro-N, N'-bis[(dimethylamino)methylene]-1,3-benzenedisulfonamide (35 mmol) and molecular sieves in absolute ethanol is added anhydrous HCl. The mixture is heated at reflux for 24 hours, cooled to room temperature, filtered and the volatiles are removed in vacuo. The residue is purified by HPLC. The intermediate is treated with zinc and acetic acid in ethyl acetate, to remove the 2,2,2-trichloroethoxycarbonyl protecting group, and with alkali, to remove the sulfonamide protecting groups and hydrolyze the esters, thereby providing the product.

EXAMPLE 4

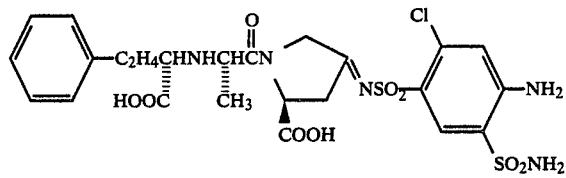

N-[N-[(1S)-1-(Hydroxycarbonyl)-3-phenylpropyl]-L-alanyl]-4-(2-chloro-4-amino-5-sulfamoylphenyl-sulfonylimino)proline To a mixture of N-[N-[(1S)-1-(ethoxycarbonyl)-3-phenylpropyl]-N-(2,2,2-trichloroethoxycarbonyl)-L-alanyl]-L-prolin-4-one ethyl ester (25 mmol), 1-(N-(2,2,2-trichloroethoxycarbonyl)amino)-3-chloro-4,6-benzenedisulfonamide (55 mmol) and molecular sieves in absolute ethanol is added anhydrous HCl. The mixture is heated at reflux overnight, cooled to room temperature, filtered, and the volatiles are removed in vacuo. The residue is purified by HPLC. The 2,2,2-trichloroethoxycarbonyl protecting groups are removed with zinc and acetic acid in ethyl acetate and the esters are hydrolyzed with alkali to give the product.

EXAMPLE 5

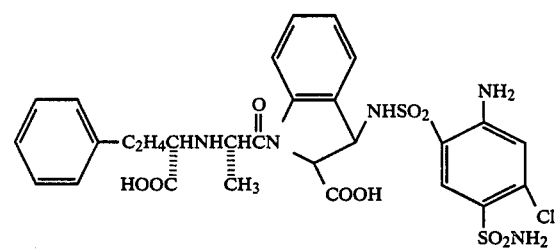

N-[N-[(1S)-1-(Hydroxycarbonyl)-3-phenylpropyl]-L-alanyl]-3-[[(2-amino-4-chloro-5-sulfamoylphenyl)sulfonyl]amino]-2,3-dihydroindole-2-carboxylic acid To a solution of N-[(1S)-1-(ethoxycarbonyl)-3-phenylpropyl]-N-(2,2,2-trichloroethoxycarbonyl)-L-alanine (2 mmol) in methylene chloride at 0° C. is added 1,1'-carbonyldiimidazole (2 mmol). The mixture is stirred 30 minutes and 3-[[(2-(N-2,2,2-trichloroethoxycarbonyl)amino-4-chloro-5-sulfamoylphenyl)sulfonyl]amino]-2,3-dihydroindole- 2-carboxylic acid ethyl ester (2.1 mmol) is added. The mixture is warmed to room temperature, stirred overnight, and the volatiles are removed in vacuo. Purification of the residue on HPLC provides the intermediate amide. The 2,2,2-trichloroethoxycarbonyl protecting group are removed with zinc and acetic acid and the esters are hydrolyzed with alkali to provide the product.

EXAMPLE 6

N-[N-[(1S)-1-(Hydroxycarbonyl)-3-phenylpropyl]-L-alanyl]-3-(2,4-disulfamoyl-5-chloroanilino)-2,3-dihydroindole-2-carboxylic acid To a solution of N-[(1S)-1-(ethoxycarbonyl)-3-phenylpropyl]-N-(2,2,2-trichloroethoxycarbonyl)-L-alanine (5 mmol) in methylene chloride at 0° C. is added 1,1'-carbonyldiimidazole (5.5 mmol). The mixture is stirred 30 minutes and 3-(2,4-disulfamoyl-5-chloroanilino)-2,3-dihydroindole-2-carboxylic acid ethyl ester (6 mmol) is added. The mixture is warmed to room temperature, stirred overnight and the volatiles are removed in vacuo. Purification of the residue on HPLC provides the intermediate amide. The 2,2,2-trichloroethoxycarbonyl protecting group is removed with zinc and acetic acid and the esters are hydrolyzed with alkali to provide the product.

EXAMPLE 7

A.

(4S)-1-((2S)-2-(N-((1S)-1-Ethoxycarbonyl-3-phenylpropyl)-N-(2,2,2-trichloroethoxycarbonyl)amino)propionyl)-4-(4-chloro-2-(furfurylamino)-5-sulfonamidobenzoyl)aminoproline ethyl ester A stirred solution of 11.3 g (0.025 mol) of N-((1S)-1-ethoxycarbonyl-3-phenylpropyl)-N-(2,2,2-trichloroethoxycarbonyl)-alanine in 200 ml $CH_2Cl_2$ is treated with 5 drops DMF, followed by a solution of 10 ml (0.12 mol) of oxalyl chloride in 50 ml $CH_2Cl_2$ added dropwise. The resulting solution is stirred for one hour after gas evolution ceases, then concentrated in vacuo. The residue is redissolved in 100 ml $CCl_4$, decanted from a small amount of red oil, and concentrated again in vacuo.

A solution of 9.4 g (0.020 mol) of (4S)-4-(4-chloro-2-(furfurylamino)-5-sulfonamidobenzoyl)aminoproline ethyl ester and 2.5 g (0.025 mol) triethylamine in 200 ml $CH_2Cl_2$ is stirred in an ice bath while a solution of the above acid chloride in 100 ml $CH_2Cl_2$ is added dropwise. The mixture is allowed to reach room temperature overnight, then washed with dilute acid and dried. The solution is concentrated in vacuo and chromatographed on silica gel to afford the desired amide.

B.

(4S)-1-((2S)-2-(N-((1S)-1-Ethoxycarbonyl-3-phenylpropyl)amino)propionyl)-4-(4-chloro-2-(furfurylamino)-5-sulfonamidobenzoyl)aminoproline ethyl ester To a solution of 9.4 g (10.5 mmol) of the above acylproline derivative in a mixture of 100 ml EtOH and 50 ml HOAc is added 6.5 g (0.10 mol) zinc dust. The resulting slurry is stirred at room temperature until TLC shows complete disappearance of starting material. Zinc salts and unreacted metal are filtered off and the filtrate concentrated in vacuo. Rapid chromatography on silica gel provides the pure amine.

C.
(4S)-1-((2S)-2-(N-((1S)-1-Hydroxycarbonyl-3-phenyl-propyl)amino)propionyl)-4-(4-chloro-2-(fur-furylamino)-5-sulfonamidobenzoyl)aminoproline To an ice-cooled solution of 3.5 g (4.79 mmol) of the above diester in 50 ml EtOH is added dropwise 25 ml 1N NaOH. The bath is removed and the solution stirred until TLC indicates complete ester hydrolysis. The solution is carefully neutralized with 1N HCl, then concentrated in vacuo and chromatographed on silica gel to give the desired product.

EXAMPLE 8

A.
(4S)-1-((2S)-2-(N-((1S)-1-Ethoxycarbonyl-3-phenyl-propyl)-N-(2,2,2-trichloroethoxycarbonyl)amino(pro-pionyl)-4-(4-amino2-chloro-5-sulfonamidobenzenesul-tonyl)aminoproline ethyl ester A crude acid chloride is prepared from 5.22 g (11.5 mmol) of N-((1S)-1-ethoxycarbonyl-3-phenylpropyl)-N-(2,2,2-trichloroethoxycarbonyl)alanine as described in Example 7A. This is dissolved in 25 ml CH$_2$Cl$_2$ and added dropwise to an ice-cooled solution of 4.3 g (10.1 mmol) of (4S)-4-(4-amino-2-chloro- 5-sulfonamidoben-zenesulfonyl)aminoproline ethyl ester and 1.5 g (14.8 mmol) of triethylamine in 150 ml CH$_2$Cl$_2$. The reaction is stirred overnight at room temperature, then worked up as in Example 7A and chromatographed to give the title amide.

B.
(4S)-1-((2S)-2-(N-((1S)-1-Ethoxycarbonyl-3-phenyl-propyl)amino)propionyl)-4-(4-amino-2chloro-5-sul-fonamidobenzenesulfonyl)aminoproline ethyl ester A solution of 4.3 g (5.0 mmol) of product 8A in 50 ml EtOH is treated sequentially with 25 ml HOAc and 4.2 g (66 mmol) of zinc dust. The reaction is stirred at room temperature until complete, as determined by TLC, then worked up as described in Example 7B to provide the desired amine.

C.
(4S)-1-((2S)-2-(N-((1S)-1-Hydroxycarbonyl-3-phenyl-propyl)amino)propionyl)-4-(4-amino-2-chloro-5-sul-fonamidobenzenesolfonyl)aminoproline A solution of 2.5 g (3.6 mmol) of product 8B in 35 ml EtOH is hydrolyzed with 15 ml 1N NaOH as described in Example 7C. Neutralization and chromatography of the crude product gives the pure diacid.

EXAMPLE 9

A. Ethyl (1S,3S)-1-(4-chloro-3-sulfonamidobenzoylamino)meth-yl-2-((2S)-N-(1S)-1-ethoxycarbonyl-3-phenylpropyl)-N-(2,2,2-trichloroethoxycarbonyl)amino)-propionyl-1,2,3,4-tetrahydroisoquinoline-3-carboxylate A solution of acid chloride, prepared from N-((1S)-1-ethoxycarbonyl-3-phenylpropyl)-N-(2,2,2-trichloroe-thoxycarbonyl)alanine as in Example 7A, in CH$_2$Cl$_2$ is added dropwise to an ice-cooled, stirred solution of (1S,3S)-1-(4-chloro-3-sulfonamidobenzoylamino)me-thyl1,2,3,4-tetrahydroisoquinoline-3-carboxylic acid ethyl ester and triethylamine in CH$_2$Cl$_2$. The reaction is stirred at room temperature overnight, then worked up as in Example 7A. Chromatography of the residue gives the desired product.

B.
Ethyl(1S,3S)-1-(4-chloro-3-sulfonamidobenzoylamino)-methyl-2-((1S)-N-((1S)-1-ethoxycarbonyl-3-phenyl-propyl)amino)-propionyl-1,2,3,4-tetrahydroisoquino-line-3-carboxylate A solution of compound 9A in EtOH is treated with 25 ml HOAc, followed by zinc dust. The resulting slurry is stirred at room temperature until TLC shows the absence of starting material. The reaction is then filtered and concentrated in vacuo. Chromatography on silica gel gives the pure amine.

C.
(1S,3S)-1-(4-chloro-3-sulfonamidobenzoylamino)meth-yl-2-((2S)-N-((1S)-1-hydroxycarbonyl-3-phenylpropyl-)amino-propionyl-1,2,3,4-tetrahydroisoquinoline-3-car-boxylic acid A solution of the above diester in EtOH is cooled in ice and treated with 1N NaOH. The resulting solution is stirred at room temperature. When TLC indicates complete conversion to diacid the mixture is carefully neutralized with dilute acid and concentrated in vacuo. Chromatography of the residue provides the pure diacid.

EXAMPLE 10

A.
1-((2S)-2-(N-((1S)-1-Ethoxycarbonyl-3-phenylpropyl-)amino)propionyl)-4-(2,3-dichloro-4-((ethoxycarbonyl)-methoxy)benzoyl)methyleneproline ethyl ester The acid chloride of N-((1S)-1-ethoxycarbonyl-3phenylpropyl)-N-(2,2,2-trichloroethoxycarbonyl)ala-nine (Example 7A) is dissolved in CH$_2$Cl$_2$ and added dropwise to a solution of 4-(2,3-dichloro-4-((ethoxycar-bonyl)methoxy)benzoyl)methylene proline ethyl ester and triethylamine in CH$_2$Cl$_2$. Further reaction and puri-fication as in example 7A gives the desired amide.

This is dissolved in EtOH and treated with HOAc and zinc dust. The reaction is stirred at room tempera-ture until starting material is consumed (TLC), then worked up as described for Example 7B. Careful chro-matography on silica gel then gives the pure amine.

B.
1-((2S)-2-(N-((1S)-1-Hydroxycarbonyl-3-phenyll-propyl)amino)propionyl)-4-(2,3-dichloro-4-(hydrox-ycarbonylmethoxy)benzoyl)methyleneproline A solution of the above triester (10A) in EtOH is cooled in ice and treated with 10% NaOH. The mixture is stirred until TLC shows complete conversion to tri-acid, then worked up and purified according to Exam-ple 7C to give the desired product.

EXAMPLE 11

1-((2S)-2-(N-((1S)-1-Hydroxycarbonyl-3-phenylpropyl-)amino)propionyl-4-ethoxy-4-(5-chloro-2,4-disulfonamidophenyl)aminopro-line 4-Ethoxy-4-(5-chloro-2,4-disulfonamidophenyl-)aminoproline ethyl ester is treated with the acid chlo-ride of N-((1S)-1-ethoxycarbonyl-3- phenylpropyl)-N-(2,2,2-trichloroethoxycarbonyl)alanine as per Example 7A. Further deprotection (Example 7B) and hydrolysis (Example 7C) as previously described gives the desired product.

EXAMPLE 12

A.
N-[N-(2,2,2-trichloroethoxycarbonyl)-N-[(1S)-1-(ethoxycarbonyl)-3-phenylpropyl]-L-alanyl]-4-[2-(3-sulfamoyl-4-chlorobenzoyl)hydrazin-1-yl]-L-proline ethyl ester To a solution of N-[N-(2,2,2-trichloroethoxycarbonyl)N-[(1S)-1-(ethoxycarbonyl)-3-phenylpropyl]-L-alanyl]-L-prolin-4-one ethyl ester (3.90 g, 6.57 mmol) in 40 ml ethanol (absolute) at 0°–5° C. was added 3-sulfamoyl-4-chlorobenzoylhydrazine (1.63 g, 6.67 mmol). The mixture was stirred 3 hours at 0°–5° C. and sodium tetrahydridoborate (0.744 g, 19.7 mmol) was added portionwise. The mixture was stirred 45 minutes at 0°–5° C. and water and ethyl acetate were added. The organic layer was washed with brine, dried (MgSO₄) and the volatiles were removed in vacuo. Purification of the residue on HPLC, using 25% hexanes in ethyl acetate as eluents, provided 2.82 g of the solid product (12-A), N-[N-(2,2,2-trichloroethoxycarbonyl)-N-[(1S)-1-(ethoxycarbonyl)-3-phenylpropyl]-L-alanyl]-4-[2-(3-sulfamoyl-4-chlorobenzoyl)hydrazin-1-yl]-L-proline ethyl ester.

B.
N-[N-[(1S)-1-(Hydroxycarbonyl)-3-phenylpropyl]-L-alanyl]-4-[2-(3-sulfamoyl-4-chlorobenzoyl)hydrazin-1-yl]-L-proline hydrochloride To a solution of compound (12-A) (2.70 g, 3.26 mmol) in 20 ml ethanol (absolute) and 10 ml acetic acid was added zinc dust (2.12 g, 32.6 mmol). The mixture was stirred 3 hours, filtered through Celite, diluted with ethyl acetate, washed with water and brine and dried (MgSO₄) Removal of the volatiles in vacuo provided a residue which was purified by HPLC using ethyl acetate as eluent. To the intermediate diester in 5 ml ethanol at 0°–5° C. was added aqueous sodium hydroxide (10 molar equivalents of sodium hydroxide). The mixture was slowly warmed to room temperature and stirred overnight. The mixture was cooled with an ice bath, acidified to pH 1 with concentrated hydrochloric acid and extracted with ethyl acetate and ethanol (95:5). The organic layers were combined, washed with brine and dried (MgSO₄). Removal of the volatiles in vacuo provided a residue which was purified by trituration with acetonitrile to provide N-[N-[(1S)-1-(hydroxycarbonyl)-3-phenylpropyl]-L-alanyl]-4-[2-(3-sulfamoyl-4-chlorobenzoyl)hydrazin-1-yl]proline hydrochloride. M.p. 188° C. (dec). This compound is a potent inhibitor of the angiotensin-converting enzyme.

EXAMPLE 13

A.
(4RS)-N-(N-((1S)-1-Ethoxycarbonyl-3-phenylpropyl)-L-alanyl-4-((N-methyl-N-((6-chloro-7-sulfamyl-3,4dihydro2H-1,2,4-benzothiadiazin-1,1-dioxide-3-yl)methyl)amino)proline ethyl ester (13-A)

To a solution of 3.7 g (8.2 mmol) of N-(N-((1S)1-ethoxycarbonyl-3-phenylpropyl)-L-alanyl)-L-proline-4-one ethyl ester hydrochloride and 3.6 g (9.5 mmol) of 3-(methylamino)methyl-6-chloro-7-sulfamyl-3,4-dihydro-2H-1,2,4-benzothiadiazine-1,1-dioxide hydrochloride in 25 ml of DMF was added 4 g MgSO₄. The mixture was stirred for 30 minutes at room temperature, then treated with a solution of 0.6 g (0.01 mol) sodium cyanoborohydride in 5 ml DMF. After stirring overnight, the mixture was partitioned between water and EtOAc, the aqueous phase washed with EtOAc, then CH₂Cl₂ and the combined organics washed with H₂O and brine.

The combined organic extracts were stirred with 2.3 g oxalic acid overnight and the resulting paste rinsed with dry EtOAc. The precipitate was redissolved in water, neutralized with excess K₂CO₃, and extracted with two portions of EtOAc. The extracts were concentrated in vacuo to give 1.7 g (28%) of product (13-A) as a mixture of diastereomers, m.p. 79–85.

B.
(4RS)-N-(N-((1S)-1-Hydroxycarbonyl-3-phenylpropyl)-L-alanyl)-4-((N-methyl-N-(6-chloro-7-sulfamyl-3,4-dihydro2H-1,2,4-benzothiadiazine-1,1-dioxide-3-yl)methyl)amino)proline (13-B)

The diester (13-A), (1.7 g, 2.3 mmol) was stirred in 10 ml 50% EtOH and treated with 10 ml 5% NaOH. After 2 hours, TLC indicated complete hydrolysis. The mixture was acidified with 8 ml 2N HCl. The resulting precipitate was washed with water, redissolved in 35 ml 0.5 N HCl, washed with 10 ml EtOAc, and lyophilized. The residue was chromatographed on silica gel to give 1.1 g (72%) of compound (13-B), m.p. 193–197. This compound is a potent inhibitor of the angiotensin-converting enzyme.

EXAMPLE 14

(4R)-4-[5-(Sulfamoyl)-4-chloro-2-[(2-furanylmethyl)amino]benzoxy]-N-[N-[(1S)-1-(hydroxycarbonyl)-3phenylpropyl]L-alanyl]-L-proline A mixture of furosemide (2.9 g, 8.8 mmol) and 1,140-carbonyldiimidazole (1.57 g, 9.7 mmol) in 30 ml anhydrous tetrahydrofuran (THF) was stirred at 25° C. for 1 hour. A solution of (4R)-N-[N-[(1S)-1-(ethoxycarbonyl)-3-phenylpropyl]L-alanyl]-4-hydroxy-L-proline ethyl ester 4-hydroxy-:-proline ethyl ester (3.7 g, 8.8 mmol) in 40 ml THF was added. The solution was heated at reflux for 20 hours, cooled to room temperature and the volatiles were removed in vacuo. The residue was diluted with ethyl acetate, washed with water, aqueous HCl and brine and dried (MgSO₄). Removal of the volatiles in vacuo and purification of the residue by HPLC, using 50% ethyl acetate in hexanes as eluents, provided the solid prouduct. The ethyl esters can be hydrolyzed with alkali and the product purified on reverse phase silica gel using water in acetonitrile as eluents.

The following compounds within the scope of this invention have also been made following the procedures described herein, and have been found to be potent inhibitors of the angiotensin-converting enzyme;

EXAMPLE 15

N-[N-[(1S)-1-hydroxycarbonyl-3-phenylpropyl]-L-alanyl]-4-[((6-chloro-2H-1,2,4-benzothiadiazin-1,1-dioxide-7yl)sulfmyl)amino]-L-proline

EXAMPLE 16

N-[N-[(1S)-1-hydroxycarbonyl-3-phenypropyl]-L-alanyl-4-[2-(6-chloro-7-sulfamoyl-3,4-dihydro-2H-1,2,4-benzothiadiazin-1,1-dioxide-3-yl)ethoxy]proline

What is claimed is:

1. A compound of the formula wherein

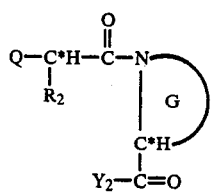

a pharmaceutically acceptable salt thereof;

Q is $Y_1$-C(O)-C*H($R_1$)NH-, -$NH_2$, $R_1$-C(O)S(C*H($R_1$))$_{0-1}$-, or HS-(C*H($R_1$))$_{0-1}$-;

$Y_1$ and $Y_2$ are independently -OH, -OR, or -$NR_1R_2$; G is

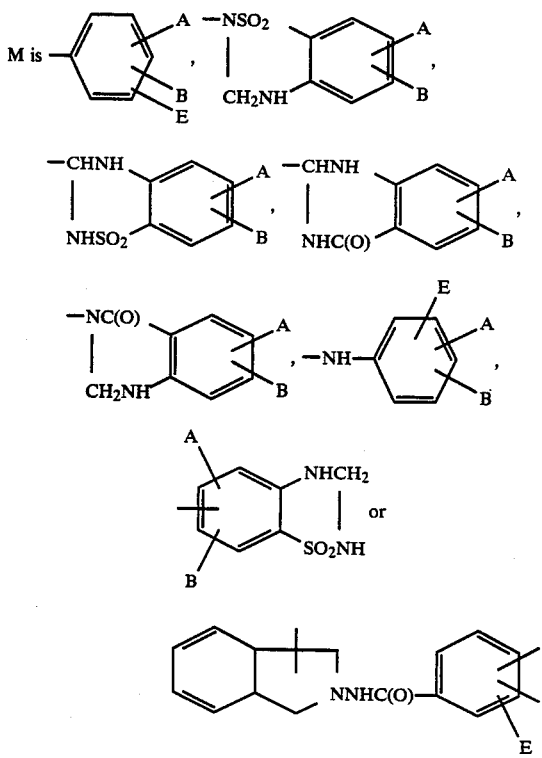

in which $G_1$ is H, -OH, $C_{1-6}$ alkyl, or $C_{1-6}$ alkoxy,

Z is —CH=(CH$_2$)$_i$C(O)M, —(CH$_2$)$_i$C(O)M, —(CH$_2$)$_i$—N(R$_3$)—C(O)—M, —(CH$_2$)$_i$C(O)—N(R$_3$)M, —(CH$_2$)$_i$SO$_2$M,—CH$_2$)$_i$ N(R$_3$)M, —O(CH$_2$)$_i$C(O)M,——(CH$_2$)$_i$—N(R$_3$)—SO$_2$—M, —(CH$_2$)$_i$M, —N(R$_3$)—CH$_2$(CH$_2$)$_i$N(R$_3$)M, —O(CH$_2$)$_i$M,=N(CH$_2$)$_i$SO$_2$M, =N(CH$_2$)$_i$M, =CH(CH$_2$)$_i$M, or —CH=CHM, wherein i is 0 to 6 inclusive provided that one carbon atom of a—(CH$_2$)$_i$—linkage can be substituted with a straight or branched-chain alkyl group of up to 3 carbon atoms;

M is

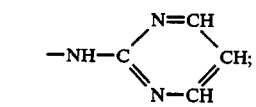

wherein A, B and E are independently H, $C_{1-6}$ alkyl, phenyl, benzyl, phenoxy, nitroalkylamino, alkanoylamino, alkanoylaminoalkyl, nitro, —OCH$_2$COOH, halogen, hydroxy, —CF$_3$, —SR, —OR, —NR$_1$R$_2$, —C(O)NR$_1$(R$_2$), —C(O)Y$_1$, —SO$_2$R, —SO$_2$NR$_1$R$_2$, or furfurylamino, provided that at least one of A and B is not hydrogen; and R, R$_1$, R$_2$, and R$_3$ in each occurrence, are independently hydrogen, alkyl having 1 to 8 carbon atoms, aryl having up to 12 carbon atoms, aryl-alkyl wherein the aryl moiety has up to 10 carbon atoms and the alkyl moiety has 1 to 6 carbon atoms, fused cycloalkylaryl being indolyl, indolinyl, indanyl, naphthyl, tetrahydronaphthyl, or decahydronaphthyl, or an alkyl group having 1 to 6 carbon atoms which is substituted with —NH$_2$, —NH—C(NH$_2$)=NH, or

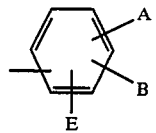

wherein the alkyl, cycloalkyl, aryl, and fused arylcycloalkyl groups may carry substituents selected from the group consisting of alkoxy with 1 to 6 carbon atoms, —CF$_3$, —OH, —SH, halogen, —NO$_2$, and —COOR.

2. A compound or salt according to claim 1 wherein Q is $Y_1$C(O)C*H($R_1$)NH—, and $Y_1$ and $Y_2$ are independently —OH, alkoxy having 1 to 8 carbon atoms, or phenyl-C$_{1-6}$-alkoxy.

3. A compound or salt according to claim 2 wherein $R_1$ is H, alkyl, or phenyl-alkyl.

4. A compound or salt according to claim 3 wherein $R_2$ is H, alkyl, or amino-alkyl.

5. A compound or salt according to claim 4 wherein G is a proline ring.

6. A compound or salt according to claim 5 wherein M is

7. The compound according to claim 6 which is N-[N-[(1S)-1-(hydroxycarbonyl)-3-phenylpropyl]-L-alanyl]-4-(2,4-disulfamoyl-5-chloroanilino)proline or a pharmaceutically acceptable acid addition alkali metal, or alkaline earth metal salt thereof.

8. The compound according to claim 6 which is N-[N-[(1S)-1-(hydroxycarbonyl)-3-phenylpropyl]-L-alanyl]-4-[[(2-amino-4-chloro-5-sulfamoylphenyl)sulfonyl]amino ]proline or a pharmaceutically acceptable acid addition alkali metal, or alkaline earth metal salt thereof.

9. The compound according to claim 6 which is N-[N-[(1S)-1-(hydroxycarbonyl)-3-phenylpropyl]-L-alanyl]-4-(2,4-disulfamoyl-5-chlorophenylimino)proline or a pharmaceutically acceptable acid addition alkali metal, or alkaline earth metal salt thereof.

10. The compound according to claim 6 which is N-[N-[(1S)-1-(hydroxycarbonyl)-3-phenylpropyl]-L-alanyl]-4-(2-chloro-4-amino-5-sulfamoylphenylsulfonylimino)proline or a pharmaceutically acceptable acid addition alkali metal, or alkaline earth metal salt thereof.

11. The compound according to claim 6 which is (4S)-1-((2S)-2-(N-(1S)-1-hydroxycarbonyl-3-phenyl-propyl)aminopropionyl)-4-(4-chloroa-2-(furfurylamino)-5-sulfonamidobenzoyl)amino proline or a pharmaceutically acceptable acid addition alkali metal, or alkaline earth metal salt thereof.

12. The compound according to claim 6 which is (4S)-1-((2S)-2-(N-((1S)-1-hydroxycarbonyl-3-phenyl-propyl)amino)propionyl)-4-(4-amino-2 -chloro-5-sulfonamidobenzonesulfonyl)aminoproline or a pharmaceutically acceptable acid addition, alkali metal, or alkaline earth metal salt thereof.

13. The compound according to claim 6 which is 1-((2S)-2-(N-((1S)-1-hydroxycarbonyl-3-phenylpropyl-)amino)propionyl)-4-(2,3-dichloro-4-(carboxymethoxy)benzoyl)methyleneproline or a pharmaceutically acceptable acid addition, alkali metal, or alkaline earth metal salt thereof.

14. The compound according to claim 6 which is 1-((2S)-2-(N-((1S)-1-hydroxycarbonyl-3-phenylpropyl-)amino)propionyl-4-ethoxy-4-(5-chloro-2,4-disulfonamido phenyl)aminoproline or a pharmaceutically acceptable acid addition, alkali metal, or alkaline earth metal salt thereof.

15. The compound according to claim 5 which is N-[N-[(1S)-1-hydroxycarbonyl-3-phenylpropyl]-L-alanyl]-4-[2-(6-chloro-7-sulfamoyl-3,4-dihydro-2H-1,2,4-benzothiadiozin1,1-dioxide-3-yl)ethoxy]proline or a pharmaceutically acceptable acid addition, alkali metal, or alkaline earth metal salt thereof.

16. The compound according to claim 5 which is (4R)-4-[5-(sulfamoyl)-4-chloro-2-8 (2-furanylmethyl-)amino]-benzoxy]-N-[N-[(1S)-1-(hydroxycarbonyl)-ethoxycarbonyl-3phenyl propyl]L-alanyl]-L-proline and its pharmaceutically acceptable salts.

17. The compound according to claim 5 which is (4R)-4-[5-(sulfamoyl)-4-chloro-2-[(2-furanylmethyl-)amino]-benzoxy]-N-[N-(1S)-1-( ethoxycarbonyl)-3phenyl propyl]L-alanyl]L-proline ethyl ester and its pharmaceutically acceptable salts.

18. A compound of salt according to claim 1 wherein Q is $Y_1$—C(O)—C*H ($R_1$)NH—, —$NH_2$, $R_1$—C-(O)S(C*H($R_1$))$_{0-1}$—, or HS—(C*H($R_1$))$_{0-1}$—;
$Y_1$ and $Y_2$ are independently —OH, —OR, or —$NR_1R_2$;
G is

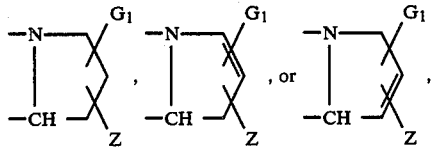

in which $G_1$ is H, —OH, $C_{1-6}$ alkyl, or $C_{1-6}$ alkoxy, Z is =CH—(CH$_2$)$_i$C(O)M, —(CH$_2$)$_i$C(O)M, —(CH$_2$-)$_i$—N(R$_3$)—C(O)—M, —(CH$_2$)$_i$C(O)—N(R$_3$)M, —(CH$_2$)$_i$SO$_2$M, —(CH$_2$)$_i$N(R$_3$)M, —O(CH$_2$)$_i$C-(O)M, —(CH$_2$)$_i$—N(R$_3$)—SO$_2$—M, —(CH$_2$)$_i$M, —N(R$_3$)—CH$_2$(CH$_2$)$_i$N(R$_3$)M, —O(CH$_2$)$_i$M, =N(CH$_2$)$_i$SO$_2$M, =N(CH$_2$)$_i$M, =(CH(CH$_2$)$_i$M, or —CH=CHM,
wherein i is 0 to 6 inclusive provided that one carbon atom of a —(CH$_2$)$_i$—linkage can be substituted with a straight or branched-chain alkyl group of up to 3 carbon atoms;

M is 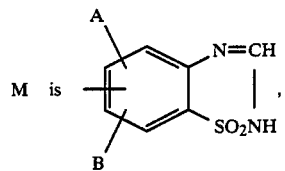

wherein A and B are independently H, $C_{1-6}$ alkyl, phenyl, benzyl, phenoxy, nitroalkylamino, alkanoylamino, alkanoylaminoalkyl, nitro, —OCH$_2$COOH, halogen, hydroxy, —CF$_3$, —SR, —OR, —NR$_1$R$_2$, —C(O)NR$_1$(R$_2$), —C(O)Y$_1$, —SO$_2$R, —SO$_2$NR$_1$R$_2$, or furfurylamino; and R, $R_1$, $R_2$, and $R_3$ in each occurrence, are independently hydrogen, alkyl having 1 to 8 carbon atoms, aryl having up to 12 carbon atoms, aryl-alkyl wherein the aryl moiety has up to 10 carbon atoms and the alkyl moiety has 1 to 6 carbon atoms, fused cycloalkylaryl being indolyl, indolinyl, indanyl, naphthyl, tetrahydronaphthyl, or decahydronaphthyl, or an alkyl group having 1 to 6 carbon atoms which is substituted with —NH$_2$, —NH—C(NH$_2$)=NH, or

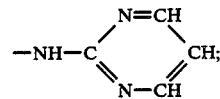

wherein the alkyl, cycloalkyl, aryl, and fused aryl-cycloalkyl groups may carry substituents selected from the group consisting of alkoxy with 1 to 6 carbon atoms, —CF$_3$, —OH, —SH, halogen, —NO$_2$, and —COOR.

19. A compound or salt according to claim 18 wherein Q is Y$_1$C(O)C*H(R$_1$)NH—, and Y$_1$ and Y$_2$ are independently —OH, alkoxy having 1 to 8 carbon atoms, or phenyl-C$_{1-6}$-alkoxy.

20. A compound or salt according to claim 19 wherein R$_1$ is H, alkyl, or phenyl-alkyl.

21. A compound or salt according to claim 20 wherein R$_2$ is H, alkyl, or amino-alkyl.

22. A compound or salt according to claim 21 wherein G is a proline ring,

23. The compound according to claim 22 which is N-[N-[(1S)-1-hydroxycarbonyl-3-phenylpropyl]-L-alanyl]-4-[((6-chloro-2H-1,2,4-benzothiadiazin-1,1-dioxide-7-yl)sulfonyl)amino]L-proline, and its pharmaceutically acceptable acid addition, alkali metal, and alkaline earth metal salts.

24. A compound or salt according to claim 1 wherein Q is Y$_1$-C(O)-C*H(R$_1$)NH—, —NH$_2$, R$_1$-C(O)S(C*H(R$_1$))$_{0-1}$-, or HS—(C*H(R$_1$))$_{0-1}$-;
Y$_1$ and Y$_2$ are independently -OH, -OR, or -NR$_1$R$_2$;
G is

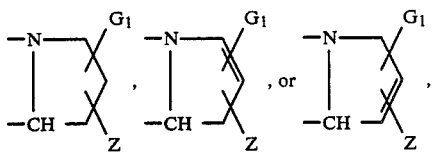

in which G$_1$ is H, -OH, C$_{1-6}$ alkyl, or C$_{1-6}$ alkoxy,

Z is $-(CH_2)_{0-6}C(O)(CH_2)_{1-6}M$, $-(CH_2)_{0-6}N(R_3)(CH_2)_{1-6}C(O)(CH_2)_{0-6}M$, $-(CH_2)_{0-6}N(R_3)C(O)(CH_2)_{1-6}M$, $-(CH_2)_{0-6}C(O)(CH_2)_{1-6}N(R_3)(CH_2)_{0-6}M$, $-(CH_2)_{0-6}C(O)N(R_3)(CH_2)_{1-6}M$, $-(CH_2)_{0-6}N(R_3)(CH_2)_{1-6}M$, $-(CH_2)_{0-6}N(R_3)SO_2(CH_2)_{1-6}M$, $-(CH_2)_{1-6}O(CH_2)_{0-6}M$, $-(CH_2)_{1-6}CH=CHM$, $-(CH_2)_{0-6}CH=CH(CH_2)_{1-6}M$,

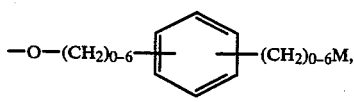

$-(CH_2)_{0-6}SO_2N(R_3)(CH_2)_{0-6}M$, $-(CH_2)_{0-6}N(R_3)(CH_2)_{0-6}N(R_3)(CH_2)_{0-6}C(O)M$; $-N(R_3)(CH_2)_{1-7}N(R_3)(CH_2)_{1-6}M$, $-(CH_2)_{1-6}N(R_3)(CH_2)_{1-7}N(R_3)(CH_2)_{0-6}M$, or $-(CH_2)_{0-6}N(R_3)N(R_3)(CH_2)_{0-6}M$, wherein one carbon atom of a $CH_2$ group can be substituted with a straight or branched-chain alkyl group having 1 to 6 carbon atoms;

M is

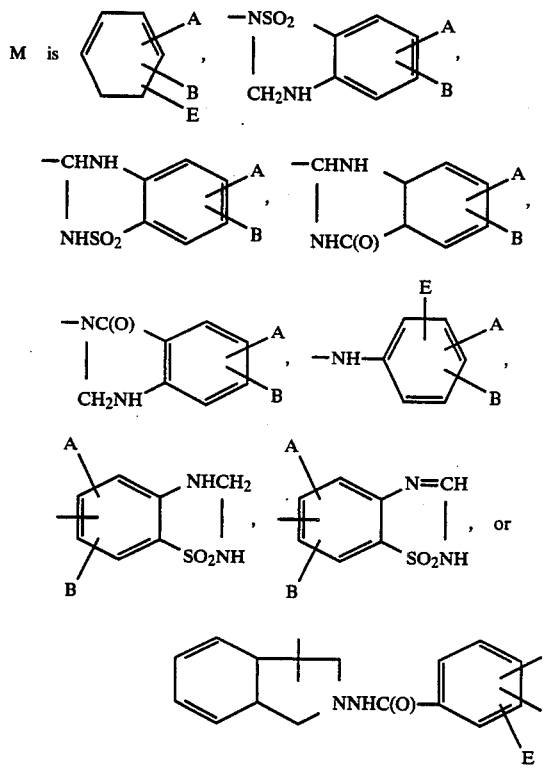

wherein A, B, and E are independently H, $C_{1-6}$ alkyl, phenyl, benzyl, phenoxy, nitroalkylamino, alkanoylamino, alkanoylaminoalkyl, nitro, $-OCH_2COOH$, halogen, hydroxy, $-CF_3$, $-SR$, $-OR$, $-NR_1R_2$, $C(O)NR_1(R_2)$, $-C(O)Y_1$, $-SO_2R$, $-SO_2NR_1R_2$, or furfurylamino, provided that at least one of A and B is not hydrogen; and R, $R_1$, $R_2$, and $R_3$ in each occurrence, are independently hydrogen, alkyl having 1 to 8 carbon atoms, aryl having up to 12 carbon atoms, aryl-alkyl wherein the aryl moiety has up to 10 carbon atoms and the alkyl moiety has 1 to 6 carbon atoms, fused cycloalkylaryl being indolyl, indolinyl, indanyl, naphthyl, tetrahydronaphthyl, or decahydronaphthyl, or an alkyl group having 1 to 6 carbon atoms which is substituted with $-NH_2$, $-NH-C(NH_2)=NH$, or

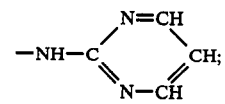

wherein the alkyl, cycloalkyl, aryl, and fused arylcycloalkyl groups may carry substituents selected from the group consisting of alkoxy with 1 to 6 carbon atoms, $-CF_3$, $-OH$, $-SH$, halogen, $-NO_2$, and $-COOR$.

25. A compound or salt according to claim 24 wherein Q is $Y_1C(O)C^*H(R_1)NH-$, and $Y_1$ and $Y_2$ are independently $-OH$, alkoxy having 1 to 8 carbon atoms, or phenyl-$C_{1-6}$-alkoxy.

26. A compound or salt according to claim 25 wherein $R_1$ is H, alkyl, or phenyl-alkyl.

27. A compound or salt according to claim 26 wherein $R_2$ is H, alkyl, or amino-alkyl.

28. A compound or salt according to claim 27 wherein G is a proline ring.

29. The compound according to claim 27 which is N-[N-[(1S)-1-hydroxycarbonyl-3-phenylpropyl]-L-alanyl]-4-[2-(3-sulfamoyl-4-chlorobenzoyl)hydrazin-1-yl]-L-proline, and its pharmaceutically acceptable acid addition, alkali metal, and alkaline earth metal salts.

30. The compound according to claim 27 which is N-[N-[(1S)-1-hydroxycarbonyl-3-phenylpropyl]-L-alanyl]-4-((N-methyl-N-(6-chloro-7-sulfamyl-3,4-dihydro-2H-1,2,4-benzothiadiazin-1,1-dioxide-3-yl)methyl)amino)proline, and its pharmaceutically acceptable acid addition, alkali metal, and alkaline earth metal salts.

31. An antihypertensive pharmaceutical preparation comprising a compound or salt according to claim 1 and a pharmaceutically acceptable carrier.

32. An anti-glaucoma pharmaceutical preparation comprising a compound or salt according to claim 1 and a pharmaceutically acceptable carrier.

33. A method of relieving hypertension in a host suffering therefrom, comprising administering to said host a therapeutically effective amount of a compound or salt according to claim 1.

34. A method of relieving elevated intraocular pressure in a host suffering therefrom, comprising administering to said host a therapeutically effective amount of a compound or salt according to claim 1.

35. A compound having the formula

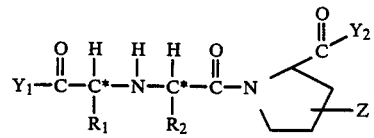

or a pharmaceutically acceptable salt thereof wherein $Y_1$ and $Y_2$ are independently $-OH$, alkoxy having 1 to 8 carbon atoms, or $NHR_2$ $R_1$ is H, $C_{1-8}$ alkyl or phenyl $C_{1-8}$ alkyl, $R_2$ is H, $C_{1-8}$ alkyl or Amino $C_{1-8}$ alkyl, and Z is

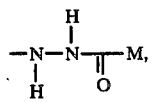
-continued
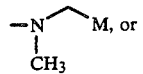
M is 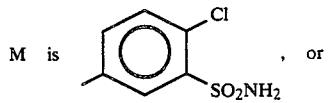, or
* * * * *